(12) United States Patent
Yoshida

(10) Patent No.: US 8,203,434 B2
(45) Date of Patent: Jun. 19, 2012

(54) WIRELESS POWER FEEDING SYSTEM AND CAPSULE ENDOSCOPE SYSTEM APPLIED WITH THE SAME

(75) Inventor: Naoki Yoshida, Nagano (JP)

(73) Assignee: Olympus Corporation, Tokyo (JP)

(*) Notice: Subject to any disclaimer, the term of this patent is extended or adjusted under 35 U.S.C. 154(b) by 991 days.

(21) Appl. No.: 11/810,115

(22) Filed: Jun. 4, 2007

(65) Prior Publication Data

US 2007/0290814 A1  Dec. 20, 2007

(30) Foreign Application Priority Data

Jun. 13, 2006 (JP) ................. 2006-163974

(51) Int. Cl.
*H04Q 5/22* (2006.01)
(52) U.S. Cl. .................................. 340/10.34
(58) Field of Classification Search .......... 340/10.2, 340/10.34, 12.38, 538.16, 854.8, 572.2, 572.6; 324/127; 341/15
See application file for complete search history.

(56) References Cited

U.S. PATENT DOCUMENTS

| | | | |
|---|---|---|---|
| 4,310,793 A | 1/1982 | Sheldrake et al. |
| 4,345,197 A | 8/1982 | Wheadon et al. |
| 4,388,618 A | 6/1983 | Finger |
| 4,536,697 A | 8/1985 | Johnston et al. |
| 4,543,521 A | 9/1985 | Morishita et al. |
| 4,651,081 A | 3/1987 | Nishimura et al. |
| 4,659,977 A | 4/1987 | Kissel et al. |
| 4,661,760 A | 4/1987 | Goto et al. |
| 4,682,097 A | 7/1987 | Matsui |
| 4,740,754 A | 4/1988 | Finger |
| 4,947,123 A | 8/1990 | Minezawa |
| 4,968,941 A | 11/1990 | Rogers |
| 5,038,728 A | 8/1991 | Yoshida et al. |
| 5,150,034 A | 9/1992 | Kyoukane et al. |
| 5,150,045 A | 9/1992 | Nagano et al. |
| 5,179,340 A | 1/1993 | Rogers |
| 5,397,991 A | 3/1995 | Rogers |
| 5,412,323 A | 5/1995 | Kato et al. |
| 5,444,378 A | 8/1995 | Rogers |
| 5,528,148 A | 6/1996 | Rogers |
| 5,602,459 A | 2/1997 | Rogers |
| 5,610,499 A | 3/1997 | Rogers |

(Continued)

FOREIGN PATENT DOCUMENTS

EP  1 487 082 A1  12/2004

(Continued)

*Primary Examiner* — Vernal Brown
(74) *Attorney, Agent, or Firm* — Scully, Scott, Murphy & Presser, P.C.

(57) ABSTRACT

A wireless power feeding system is provided, which achieves a configuration enabling effective reception of electrical energy wirelessly transmitted from a wireless power feeding device, and which contributes to the improvement of the power reception efficiency. For the above purpose, the wireless power feeding system includes a power transmitting coil for wirelessly transmitting the electrical energy, a power supply connected to the power transmitting coil, a control unit for controlling the power supply, a power receiving coil portion for receiving the electrical energy transmitted from the power transmitting coil, a power receiving circuit for supplying a load member with the electrical energy received by a power receiving coil, and a magnetic member for collecting a magnetic flux generated by the power transmitting operation of the power transmitting coil to the power receiving coil.

8 Claims, 3 Drawing Sheets

U.S. PATENT DOCUMENTS

| | | | |
|---|---|---|---|
| 7,042,196 B2 * | 5/2006 | Ka-Lai et al. | 320/108 |
| 7,145,322 B2 * | 12/2006 | Solveson et al. | 324/127 |
| 7,375,492 B2 * | 5/2008 | Calhoon et al. | 320/108 |
| 7,668,450 B2 * | 2/2010 | Todd et al. | 396/117 |
| 2005/0064815 A1 | 3/2005 | Kanazawa | |
| 2005/0154294 A1 | 7/2005 | Uchiyama et al. | |

FOREIGN PATENT DOCUMENTS

| | | |
|---|---|---|
| JP | 55-157901 A | 11/1980 |
| JP | 2001-224551 | 8/2001 |
| JP | 2002-010535 | 1/2002 |
| JP | 2005-130943 | 5/2005 |

* cited by examiner

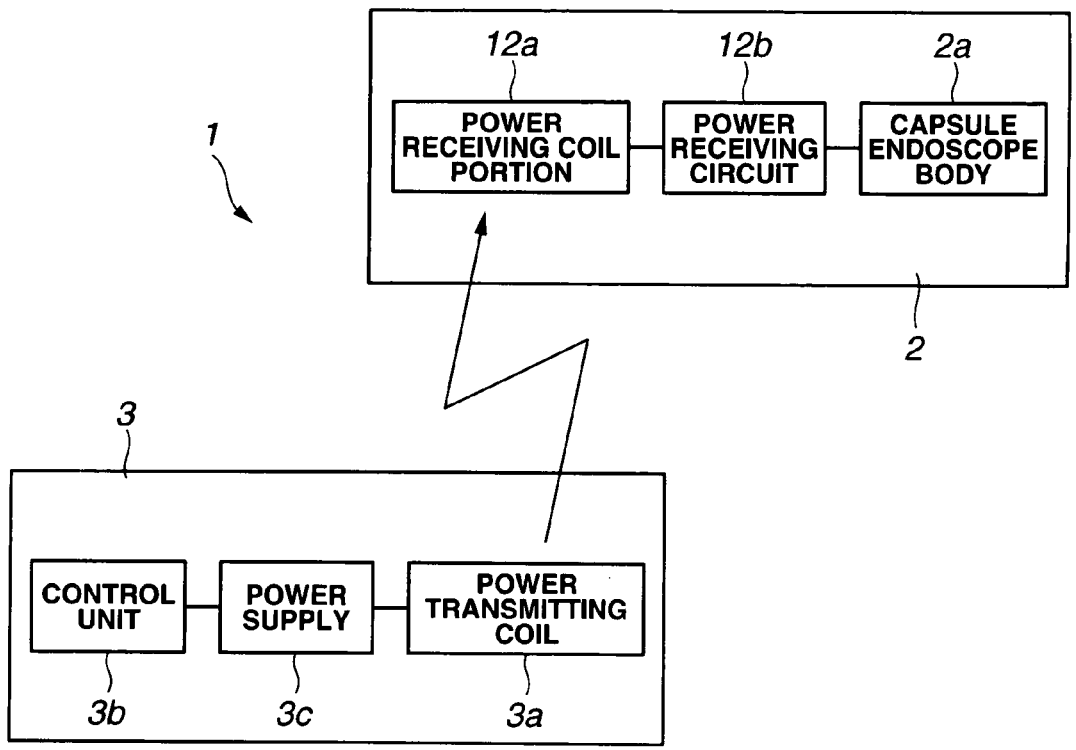
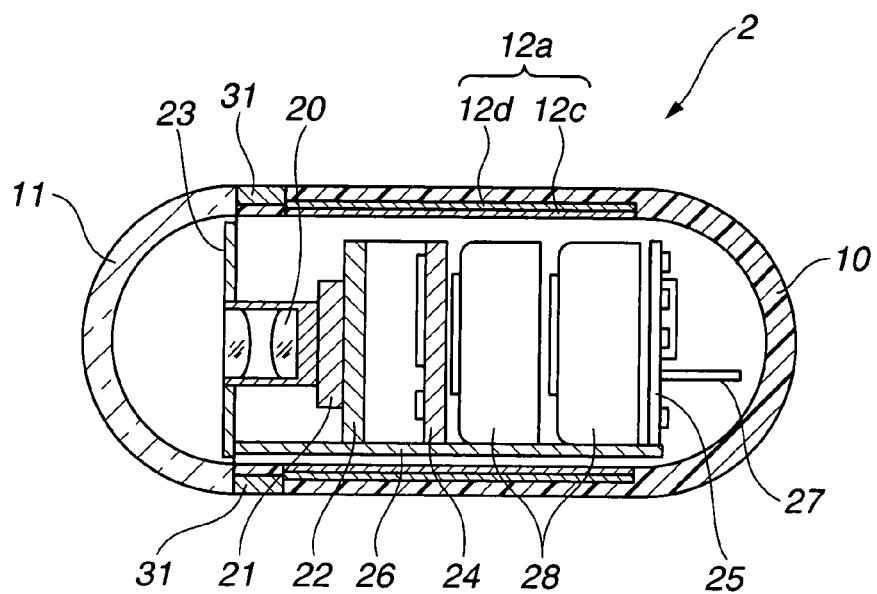

WIRELESS POWER FEEDING SYSTEM AND CAPSULE ENDOSCOPE SYSTEM APPLIED WITH THE SAME

This application claims the benefit of Japanese Application No. 2006-163974 filed in Japan on Jun. 13, 2006, the contents of which are incorporated herein by this reference.

BACKGROUND OF THE INVENTION

1. Field of the Invention

The present invention relates to a wireless power feeding system and a capsule endoscope system applied with the wireless power feeding system. More specifically, the present invention relates to a wireless power feeding system for supplying electric power in accordance with a wireless method and contributing to the improvement of the power reception efficiency of a receiver, and a capsule endoscope system applied with the wireless power feeding system.

2. Description of the Related Art

In recent years, various proposals have been made on a capsule endoscope system, which is a medical system for performing, for example, inspection of a body cavity or the like, and which is configured to include a so-called capsule endoscope and a wireless power feeding device, for example, as in Japanese Unexamined Patent Application Publication No. 2001-224551, for example. The capsule endoscope is a small-sized endoscope storing, in a capsule-shaped chassis, observation means formed by an image pickup optical system and image pickup means, illumination means, communication means, a power supply, power receiving means, and so forth. The wireless power feeding device is applied with a communication device for performing wireless communication with the capsule endoscope, recording means for recording a received signal, and a wireless power feeding system for extracorporeally supplying electrical power to the capsule endoscope by wireless or the like with the use of an AC (alternating current) magnetic field.

A capsule endoscope system disclosed in the above Japanese Unexamined Patent Application Publication No. 2001-224551 is configured to include a capsule endoscope and a wireless power feeding device, for example. The capsule endoscope includes, for example, illumination means for illuminating the interior of a living body, image pickup means for picking up an image of a region illuminated by the illumination means, a transmitting antenna for wirelessly transmitting an image signal obtained by the image pickup means to the outside of the body, and a power receiving coil for receiving electrical energy transmitted from the outside of the body. The wireless power feeding device includes, for example, a power transmitting coil for supplying the electrical energy to the capsule endoscope in accordance with a wireless power feeding method.

According to the above configuration, the electrical energy transmitted from the power transmitting coil of the wireless power feeding device is received by the power receiving coil of the capsule endoscope. Thereby, the electrical energy is fed to the capsule endoscope being used in a body cavity from the wireless power feeding device disposed outside the body.

In the above case, the capsule endoscope system has a characteristic of being capable of obtaining a good power reception efficiency in the power transmission from the wireless power feeding device to the capsule endoscope when the direction of the winding axis of the power receiving coil disposed inside the capsule endoscope matches the direction of magnetic fluxes generated from the power transmitting coil of the wireless power feeding device.

SUMMARY OF THE INVENTION

A wireless power feeding system according to one aspect of the present invention includes a power transmitting coil for wirelessly transmitting electrical energy, a power supply connected to the power transmitting coil, a control unit for controlling the power supply, a power receiving coil for receiving the electrical energy transmitted from the power transmitting coil, a power receiving circuit for supplying a load member with the electrical energy received by the power receiving coil, and a magnetic member for collecting a magnetic flux generated by the power transmitting operation of the power transmitting coil to the power receiving coil.

Further, a capsule endoscope system according to another aspect of the present invention is applied with the above-described wireless power feeding system.

The advantages of the present invention will become more clearly understood from the following detailed description.

BRIEF DESCRIPTION OF THE DRAWINGS

FIG. 1 is a block configuration diagram illustrating a basic configuration of a capsule endoscope system applied with a wireless power feeding system according to a first embodiment of the present invention;

FIG. 2 is a cross-sectional configuration diagram schematically illustrating an internal configuration of a capsule endoscope of the capsule endoscope system illustrated in FIG. 1;

DETAILED DESCRIPTION OF THE PREFERRED EMBODIMENTS

Figure 3:
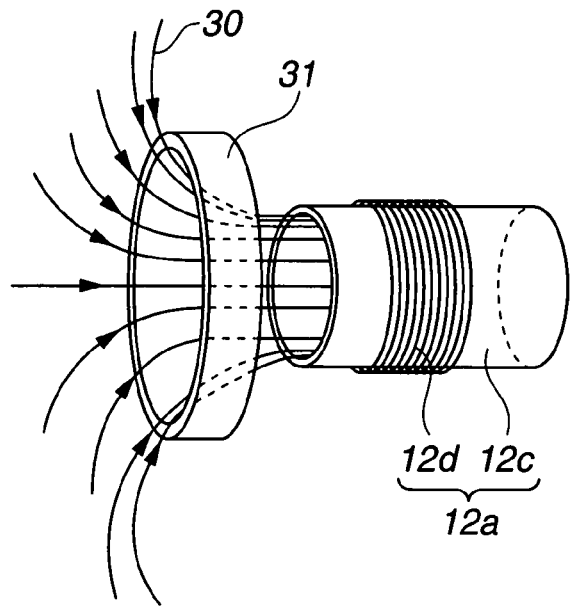
FIG. 3 is an enlarged conceptual diagram of essential parts, extracting and conceptually illustrating only parts in the vicinity of a power receiving coil portion of the capsule endoscope of the capsule endoscope system illustrated in FIG. 1.

The present invention will be described below with reference to illustrated embodiments thereof.

As illustrated in FIG. 1, a capsule endoscope system 1 applied with a wireless power feeding system according to a first embodiment of the present invention is configured to include a capsule endoscope 2 and an extracorporeal unit 3.

The extracorporeal unit 3 is configured to mainly include a power supply 3c, a control unit 3b for controlling the power supply 3c, and a power transmitting coil 3a for wirelessly transmitting electrical energy.

The power transmitting coil 3a is powered by the power supply 3c to generate an AC magnetic field. The control unit 3b controls the output from the power supply 3c to adjust the AC magnetic field generated from the power transmitting coil 3a, i.e., the transmitted electric power.

The capsule endoscope 2 is configured to mainly include, for example, a power receiving coil portion 12a, a capsule endoscope body 2a, and a power receiving circuit 12b. The power receiving coil portion 12a receives the electrical energy transmitted from the power transmitting coil 3a of the above-described extracorporeal unit 3. The capsule endoscope body 2a includes, for example, an illumination unit, an image pickup unit, and a signal processing unit. The power receiving circuit 12b receives the electrical energy received by the power receiving coil portion 12a, and supplies the electrical energy to the capsule endoscope body 2a as electric power.

As illustrated in FIG. 2, the capsule endoscope 2 is configured to include, for example, a capsule-shaped chassis member formed by a sealed capsule portion 10 and a transparent cover portion 11, and various constituent components provided inside the chassis member.

The constituent components disposed inside the chassis member include, for example, an illumination unit 23, an image pickup optical system 20, an image pickup device 21, an image pickup device drive control unit 22, a signal processing unit 24, a modulating and transmitting amplifier unit 25, a transmitting antenna unit 27, emergency batteries 28, the power receiving coil portion 12a, the power receiving circuit 12b, an electrical board 26, and a magnetic member 31. The illumination unit 23 forms illumination means for illuminating the interior of the body of a subject (a living body), and is formed by an illuminating light-emitting diode (LED), for example. The image pickup optical system 20 receives light reflected from a region illuminated by illuminating light of the illumination unit 23 to form an optical image, and forms an image of a target object on a light receiving surface of the image pickup device 21 described below. The image pickup device 21 is a photoelectric conversion device for receiving the optical image of the target object formed by the image pickup optical system 20 and performing photoelectric conversion processing to convert the optical image into an electrical signal, and is formed by an image sensor, for example. The image pickup device drive control unit 22 performs drive control of the image pickup device 21. The signal processing unit 24 forms signal processing means for receiving the electrical signal (image signal) outputted from the image pickup device 21 and performing predetermined signal processing on the electrical signal. The modulating and transmitting amplifier unit 25 modulates and amplifies the signal processed by the signal processing unit 24. The transmitting antenna unit 27 receives a signal (image signal) outputted from the modulating and transmitting amplifier unit 25 and transmits the signal to the outside of the body. The emergency battery 28 function as a power supply unit of the capsule endoscope 2. The power receiving coil portion 12a receives the electrical energy (electric power) transmitted in accordance with a wireless power feeding method from the extracorporeal unit 3 (see FIG. 1), which is a wireless power feeding device disposed outside the body. The power receiving circuit 12b (not particularly illustrated in FIG. 2, see FIG. 1) is connected to the power receiving coil portion 12a. The electrical board 26 electrically connects, for example, the image pickup device drive control unit 22, the illumination unit 23, the signal processing unit 24, and the modulating and transmitting amplifier unit 25, and is formed by a rigid board or a flexible printed board, for example.

The above-described image pickup device 21 has a function of picking up an image of the region illuminated by the illumination unit 23. The image pickup optical system 20 including the image pickup device 21, the image pickup device drive control unit 22, and so forth form image pickup means. That is, the image pickup means has a function of obtaining an electrical image signal for displaying the state inside a body cavity on an observation screen of an image display device (not illustrated) as an observed image.

Further, the modulating and transmitting amplifier unit 25 and the transmitting antenna unit 27, for example, form transmission means for transmitting the image signal obtained by the above-described image pickup means to receiving means (not particularly illustrated) of the extracorporeal unit 3 disposed outside the body. The transmission means has a function of receiving the image signal signal-processed by signal processing means (the signal processing unit 24), performing the predetermined signal processing on the image signal, and thereafter transmitting the processed image signal to the outside of the body.

As described above, the power receiving circuit 12b receives the electrical energy received by the power receiving coil portion 12a and supplies the electrical energy as the electric power for the capsule endoscope body 2a. The power receiving circuit 12b also supplies the electrical energy to the emergency batteries 28, and thus functions also as charging means for charging the emergency batteries 28. Accordingly, the present capsule endoscope 2 can store the received electrical energy in the emergency batteries 28 as electric power. As the emergency battery 28, a rechargeable battery, such as an electric double layer capacitor and a nickel metal hydride battery, for example, can be employed.

The inside of the sealed capsule portion 10 of the chassis member is provided with the power receiving coil portion 12a. The power receiving coil portion 12a is provided to receive the electrical energy transmitted from the power transmitting coil 3a of the extracorporeal unit 3. The power receiving coil portion 12a is configured to include a substantially cylindrical shaped core 12c and a coil 12d wound around the core 12c.

The above-described various constituent components are suitably disposed in a space formed inside the power receiving coil portion 12a.

Further, in the vicinity of the power receiving coil portion 12a, the magnetic member 31 of a toric shape, for example, is disposed. The magnetic member 31 is formed of a material having high magnetic permeability, such as ferrite, amorphous, and permalloy, for example. The shape of the magnetic member 31 is not limited to the toric shape. Thus, the cross-sectional shape of the magnetic member 31 may be a polygonal shape, such as a quadrangular shape and an octagonal shape, as long as the magnetic member 31 has a circular shape.

The magnetic member 31 and the power receiving coil portion 12a are disposed such that the hollow interiors thereof are consecutive to each other. In the hollow interiors, the above-described constituent components are disposed.

As illustrated in FIG. 2, in the present embodiment, the magnetic member 31 is disposed in the vicinity of and to the outside of the distal end of the sealed capsule portion 10. However, the disposition of the magnetic member 31 is not limited to such a configuration. Thus, the magnetic member 31 may be configured to be disposed in the space inside the sealed capsule portion 10.

In the thus configured capsule endoscope system 1 of the present embodiment, the image signal obtained by the image pickup operation of the image pickup means of the above-described capsule endoscope 2 is converted into data by the signal processing unit 24, and thereafter is transmitted to the extracorporeal unit 3 via the transmission means (the modulating and transmitting amplifier unit 25 and the transmitting antenna unit 27). Then, the extracorporeal unit 3 receives the image data signal.

The image data signal received by the extracorporeal unit 3 is subjected to predetermined signal processing in an internal circuit of the extracorporeal unit 3, and then is transmitted to the image display device (not illustrated). The image data signal is then subjected to predetermined signal processing in the image display device to be converted into an image signal most suitable to be displayed. Thereafter, the image signal is displayed as an image on a display unit of the image display device.

Meanwhile, the extracorporeal unit 3 transmits the electrical energy from the power transmitting coil 3a in accordance with the wireless power feeding method on the basis of the control of the power supply 3c by the control unit 3b. The power receiving coil portion 12a of the capsule endoscope 2 receives the electrical energy from the power transmitting coil 3a and transmits the electrical energy to the power receiving circuit 12b.

In the above case, magnetic fluxes 30 (see FIG. 3) generated from the power transmitting coil 3a are collected by the magnetic member 31 and interlinked with the power receiving coil portion 12a. In the present embodiment, the magnetic member 31 is configured to be disposed in the vicinity of the power receiving coil portion 12a. Thus, in addition to the magnetic fluxes 30 interlinked with the power receiving coil portion 12a, magnetic fluxes around the magnetic fluxes 30 can be also brought into the power receiving coil portion 12a, unlike a case in which the magnetic member 31 is not provided (a case in which only the power receiving coil portion 12a is provided).

Then, the electrical energy received by the power receiving coil portion 12a is fed to an electrical circuit in the present capsule endoscope 2 via the power receiving circuit 12b. Further, the received electrical energy (electric power) is supplied to the emergency batteries 28 to charge the emergency batteries 28. Accordingly, the electrical energy charged in the emergency batteries 28 is supplied to the capsule endoscope 2 to operate the capsule endoscope 2 in the event of an emergency, such as the stop of the power transmission from the power transmitting coil 3a (see FIG. 1), for example, or in a particular event.

As described above, according to the above-described first embodiment, the magnetic member 31 is provided in the vicinity of the power receiving coil portion 12a of the capsule endoscope 2. It is therefore possible to collect more of the magnetic fluxes 30 to the power receiving coil portion 12a. Accordingly, it is possible to improve the power reception efficiency of the power receiving coil portion 12a, and to supply stable electric power.

As described above, the above-described wireless power feeding system has the effect of enabling the improvement of the power reception efficiency. Thus, the power receiving coil can be configured to have a smaller diameter than in a wireless power feeding system configured not to include the magnetic member. Accordingly, in the capsule endoscope system 1 applied with the present wireless power feeding system, the external size of the capsule endoscope 2 including the power receiving coil portion 12a can be reduced. At the same time, stable drive of the capsule endoscope 2 can be achieved.

If the magnetic member 31 is configured to have a larger diameter than the diameter of the power receiving coil portion 12a, more of the peripheral magnetic fluxes can be collected. Therefore, it is desirable to set the diameter of the magnetic member 31 to be larger than the diameter of the power receiving coil portion 12a.

In the above-described first embodiment, as illustrated in FIG. 3, the single magnetic member 31 is disposed in the vicinity of the power receiving coil portion 12a of the capsule endoscope 2, as an example. However, the disposition of the magnetic member 31 is not limited to the above example. Thus, a plurality of the magnetic members 31 may be disposed, for example.

Figure 4:
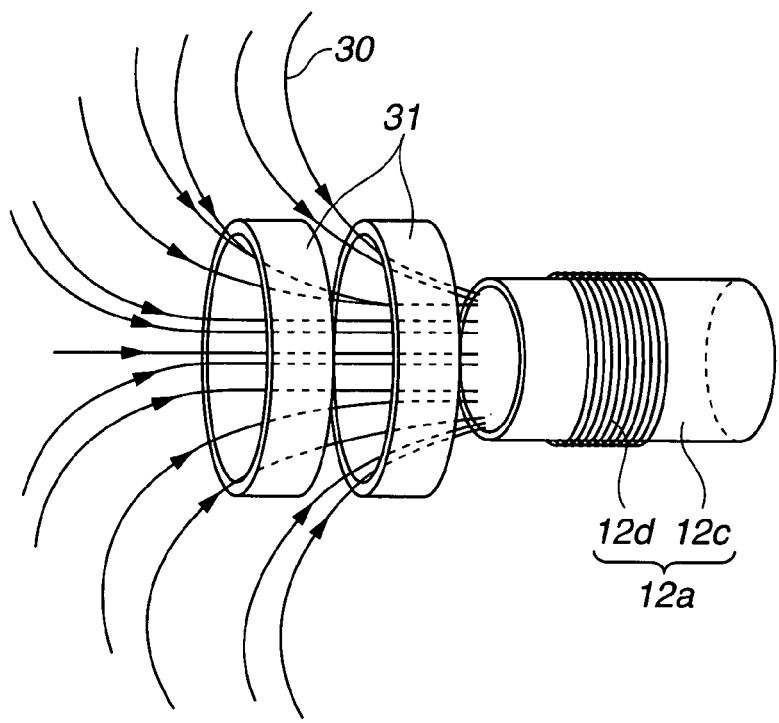
FIG. 4 is an enlarged conceptual diagram of essential parts of a first modified example of the first embodiment of the present invention, extracting and conceptually illustrating only parts in the vicinity of the power receiving coil portion of the capsule endoscope of the capsule endoscope system.

For example, in a first modified example illustrated in FIG. 4, two magnetic members 31 are disposed in a row in the vicinity of one end of the power receiving coil portion 12a.

Figure 5:
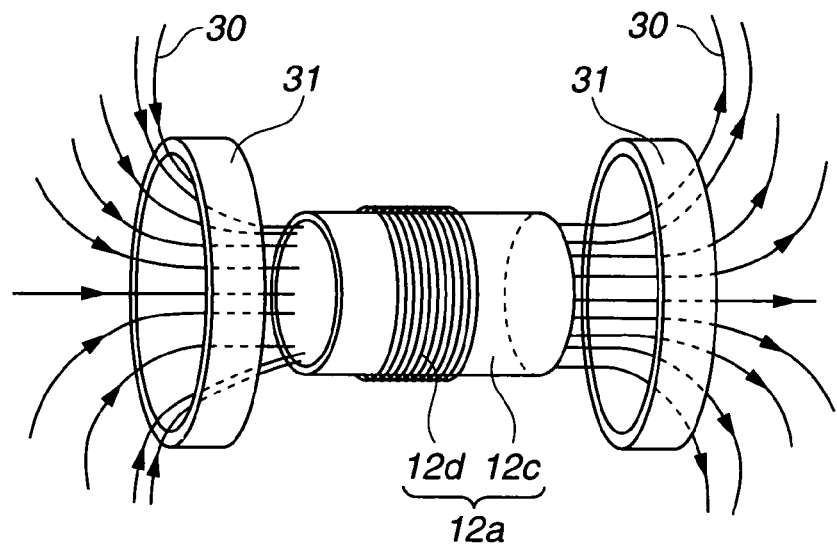
FIG. 5 is an enlarged conceptual diagram of essential parts of a second modified example of the first embodiment of the present invention, extracting and conceptually illustrating only parts in the vicinity of the power receiving coil portion of the capsule endoscope of the capsule endoscope system.

Further, in a second modified example illustrated in FIG. 5, two magnetic members 31 are disposed in the vicinity of the opposite ends of the power receiving coil portion 12a to sandwich the power receiving coil portion 12a.

In either one of the configurations of the first and second modified examples illustrated in FIGS. 4 and 5, more of the magnetic fluxes 30 can be collected than in the configuration formed by the single power receiving coil portion 12a and not provided with the magnetic member 31. Therefore, the density of the magnetic fluxes interlinked with the power receiving coil portion 12a is increased, and thus the present examples contribute to the improvement of the power reception efficiency.

Further, in the first and second modified examples illustrated in FIGS. 4 and 5, respectively, the number of the magnetic members 31 is set to be plural (two), as opposed to the above-described first embodiment. Thus, more of the magnetic fluxes 30 can be collected than in the first embodiment.

Furthermore, in the second modified example illustrated in FIG. 5, the magnetic members 31 are disposed in the vicinity of the opposite ends of the power receiving coil portion 12a. Thus, the magnetic fluxes can be collected at the two ends of the power receiving coil portion 12a. Therefore, further improvement of the power reception efficiency can be expected.

A wireless power feeding system according to a second embodiment of the present invention will now be described below.

A basic configuration of the present embodiment is substantially similar to the configuration of the above-described first embodiment. The present embodiment is different from the first embodiment only in that the magnetic member 31 is disposed in a slightly different disposition direction. Therefore, drawings and detailed description of the configurations of the present embodiment similar to the configurations of the above-described first embodiment will be omitted, and only components directly relating to the present embodiment will be described below with reference to FIG. 6.

Figure 6:
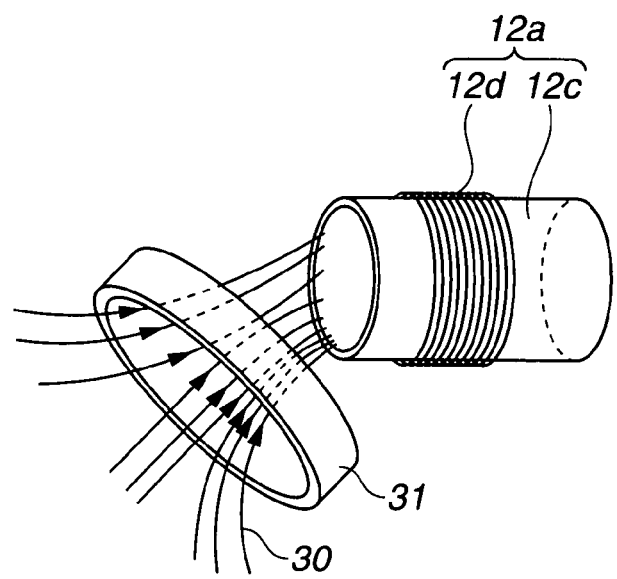
FIG. 6 is an enlarged conceptual diagram of essential parts, extracting and conceptually illustrating only parts in the vicinity of the power receiving coil portion of a capsule endoscope of a capsule endoscope system applied with a wireless power feeding system according to a second embodiment of the present invention.

As illustrated in FIG. 6, in the capsule endoscope 2 of the capsule endoscope system 1 applied with the wireless power feeding system of the present embodiment, the magnetic member 31 disposed in the vicinity of the power receiving coil portion 12a is configured such that the direction and the position thereof can be changed in the chassis member of the capsule endoscope 2.

Therefore, the capsule endoscope 2 of the present embodiment is configured to include an information detection unit for detecting the direction, the position, and the amount of the received power of the power receiving coil portion 12a, and a magnetic member control unit for changing the direction and the position of the magnetic member 31. The information detection unit and the magnetic member control unit are configured to be included in, for example, the power receiving circuit 12b or the capsule endoscope body 2a in the capsule endoscope 2. Other configurations of the present embodiment are similar to the configurations of the above-described first embodiment.

The operation of the thus configured wireless power feeding system of the present embodiment will be described below. A basic operation of the present embodiment is similar to the operation of the above-described first embodiment.

Firstly, an operation of transmitting the electric power from the extracorporeal unit 3 is started. Then, when the capsule endoscope 2 becomes operational, the information detection unit provided in the capsule endoscope 2 executes an operation of detecting the state of the power receiving coil portion 12a, i.e., the direction, the position, and the amount of the received power of the power receiving coil portion 12a.

On the basis of a result of the detection performed by the above-described information detection unit, the magnetic member control unit performs control to change the direction and the position of the magnetic member 31 so as to maximize the amount of power to be received.

For example, the capsule endoscope 2 being used in the body constantly changes the posture thereof while moving in the body cavity.

In a wireless power feeding system, the amount of power received by a power receiving coil is maximized when the winding axis of a power transmitting coil substantially matches the winding axis of the power receiving coil.

Therefore, as the amount of the received power and the direction and the position of the power receiving coil portion 12a of the capsule endoscope 2, which keeps changing the posture thereof in the body, with respect to the power transmitting coil 3a are detected by the information detection unit, and the control is performed to change the direction and the position of the magnetic member 31 on the basis of the detection result, the magnetic fluxes generated from the power transmitting coil 3a can be reliably collected to the power receiving coil portion 12a.

That is, when the winding axis of the power receiving coil portion 12a fails to match the winding axis of the power transmitting coil 3a, the direction and the position of the magnetic member 31 are changed to collect more of the magnetic fluxes so that the magnetic fluxes interlinked with the power receiving coil portion 12a can be increased.

With the direction and the position of the magnetic fluxes 31 thus changed appropriately, it is possible to effectively collect magnetic fluxes of other directions, which cannot be collected in the above-described first embodiment in which the magnetic member 31 is fixed. That is, it is possible to achieve a configuration capable of collecting more of the magnetic fluxes by performing the control to change the direction and the position of the magnetic member 31 in accordance with the posture of the capsule endoscope 2 and thus changing the state of the magnetic member 31 to maximize the amount of power to be received.

As described above, according to the present embodiment, an effect similar to the effect of the above-described first embodiment can be obtained, and further improvement of the power reception efficiency can be expected, as compared with the above-described first embodiment and respective modified examples thereof.

That is, even if the direction or the position of the capsule endoscope 2 being used in the body is changed, the power reception efficiency can be improved by changing the direction or the position of the magnetic member 31 in accordance with the change in posture of the capsule endoscope 2.

Accordingly, the wireless power feeding by the wireless power feeding system can be stabilized. Further, if the wireless power feeding system is applied to the capsule endoscope system, the capsule endoscope 2 can be more stably driven.

In the above-described respective embodiments, the wireless power feeding system of the present invention is applied to the capsule endoscope system, as an example. However, the application of the wireless power feeding system is not limited to the above example. It is needless to say that the wireless power feeding system of the present invention can be widely applied to devices which transmit and receive electric power in accordance with the wireless power feeding method.

It is also needless to say that the present invention is not limited to the above-described embodiments, and that various modifications or applications can be made within a scope not departing from the gist of the present invention.

It is obvious that, in the present invention, different embodiments can be configured in a wide range on the basis of the present invention, without departing from the spirit and the scope of the invention. The present invention is not restricted by particular embodiments thereof, except as limited by the appended claims.

What is claimed is:

1. A wireless power feeding system comprising:
    a power transmitting coil for wirelessly transmitting electrical energy;
    a power supply connected to the power transmitting coil;
    a control unit for controlling the power supply;
    a power receiving coil portion including a power receiving coil for receiving the electrical energy transmitted from the power transmitting coil, and a core around which the power receiving coil is wound, the core collecting a magnetic flux generated by the power transmitting operation of the power transmitting coil to the power receiving coil;
    a power receiving circuit for supplying a load member with the electrical energy received by the power receiving coil; and
    a magnetic member having a circular shape for collecting the magnetic flux generated by the power transmitting operation of the power transmitting coil to the power receiving coil, the magnetic member being formed as a separate member with respect to the core and arranged away from the power receiving coil and the core,
    wherein the magnetic member and the power receiving coil are disposed such that hollow interiors thereof are consecutive to each other.

2. The wireless power feeding system according to claim 1, wherein the diameter of the magnetic member is set to be larger than the diameter of the power receiving coil.

3. The wireless power feeding system according to claim 1, wherein the direction of the magnetic member can be changed.

4. The wireless power feeding system according to claim 2, wherein the direction of the magnetic member can be changed.

5. A capsule endoscope system applied with the wireless power feeding system according to claim 1.

6. A capsule endoscope system applied with the wireless power feeding system according to claim 2.

7. A capsule endoscope system applied with the wireless power feeding system according to claim 3.

8. A capsule endoscope system applied with the wireless power feeding system according to claim 4.

* * * * *